(12) United States Patent
Mehta et al.

(10) Patent No.: US 12,042,429 B2
(45) Date of Patent: Jul. 23, 2024

(54) SYSTEMS AND METHODS FOR MASS AIR FLOW CONTROL IN VACUUM BASED ASPIRATION IN SURGICAL SYSTEM

(71) Applicant: Johnson & Johnson Surgical Vision, Inc., Irvine, CA (US)

(72) Inventors: Deep Mehta, Irvine, CA (US); Sandra Keh, Irvine, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 660 days.

(21) Appl. No.: 17/330,132

(22) Filed: May 25, 2021

(65) Prior Publication Data

US 2021/0378865 A1 Dec. 9, 2021

Related U.S. Application Data

(60) Provisional application No. 63/034,919, filed on Jun. 4, 2020.

(51) Int. Cl.
*A61F 9/007* (2006.01)
*A61B 34/00* (2016.01)

(52) U.S. Cl.
CPC ...... *A61F 9/00745* (2013.01); *A61F 9/00736* (2013.01); *A61B 34/25* (2016.02); *A61B 2217/005* (2013.01)

(58) Field of Classification Search
CPC ............... A61B 2217/005; A61B 34/25; A61F 9/00736; A61F 9/00745; A61M 1/72; A61M 1/74; A61M 1/741; A61M 2205/12; A61M 2205/3331; A61M 2205/3341; A61M 2205/50; A61M 2210/0612
See application file for complete search history.

(56) References Cited

U.S. PATENT DOCUMENTS

| | | | |
|---|---|---|---|
| 5,624,394 A | 4/1997 | Barnitz et al. | |
| 6,599,277 B2 | 7/2003 | Neubert | |
| 7,524,299 B2 | 4/2009 | Hopkins et al. | |
| 8,439,874 B2* | 5/2013 | Hertweck | A61M 1/74 604/118 |
| 9,393,152 B2* | 7/2016 | Wong | A61F 9/00745 |
| 2006/0058811 A1 | 3/2006 | Kishimoto | |
| 2017/0042733 A1 | 2/2017 | Sorensen et al. | |
| 2019/0099546 A1* | 4/2019 | Keh | A61M 1/743 |

* cited by examiner

*Primary Examiner* — Quynh-Nhu H. Vu
(74) *Attorney, Agent, or Firm* — Johnson & Johnson Surgical Vision, Inc.

(57) ABSTRACT

A surgical system for the treatment of ocular problems including a surgical cassette, a surgical console operatively coupled to the surgical cassette and further including a processor, a vacuum source positioned in-line with a vacuum regulator and a mass air flow controller, and a tank fluidly connected to the mass air flow controller, wherein the processor is configured to calculate an air flow set point in accordance with a received at least one user-defined fluid flow rate set point; and wherein the mass air flow controller modulates air flow from the tank to the vacuum source in accordance with the received the air flow set point to meet a user-defined fluid flow rate.

19 Claims, 7 Drawing Sheets

SYSTEMS AND METHODS FOR MASS AIR FLOW CONTROL IN VACUUM BASED ASPIRATION IN SURGICAL SYSTEM

CROSS-REFERENCE TO RELATED APPLICATIONS

This application claims the benefit under 35 U.S.C. § 119(e) of U.S. Provisional Patent Application No. 63/034,919 filed Jun. 4, 2020, which is incorporated herein by reference in its entirety.

BACKGROUND

Field of Technology

The present disclosure relates generally to phacoemulsification surgical systems. In particular, the present disclosure relates to phacoemulsification systems including a mass air flow controller to actively vary mass air flow for various vacuum set points to achieve a user-defined fluid flow rate.

Description of the Background

Cataracts affect more than 22 million Americans age 40 and older, and as the U.S. population ages, more than 53 million Americans are expected to have cataracts by the year 2030. Cataract surgery entails the removal of a lens of an eye that has developed clouding of the eye's natural lens, or opacification. As a result of opacification, light is unable to travel to the retina, thereby causing vision loss. Once vision becomes seriously impaired, cataract surgery is a viable option with a high level of success. During cataract surgery, a surgeon replaces the clouded lens with an intraocular lens (IOL).

Certain surgical procedures, such as phacoemulsification surgery, have been successfully employed in the treatment of certain ocular problems, such as cataracts. Phacoemulsification surgery utilizes a small corneal incision to insert the tip of at least one phacoemulsification handheld surgical implement, or handpiece, through the corneal incision. The handpiece includes a needle which is ultrasonically driven once placed within the incision to emulsify the eye lens, or to break the cataract into small pieces. The broken cataract pieces or emulsified eye lens may subsequently be removed using the same handpiece, or another handpiece, in a controlled manner. The surgeon may then insert a lens implant into the eye through the incision. The incision is allowed to heal, and the result for the patient is typically significantly improved eyesight.

Currently during cataract surgery, a majority of phacoemulsification platforms provide three primary states for fluidics and phaco control: irrigation, aspiration and ultrasound with respective foot pedal zones. The foot pedal treadle position 1, correlates to irrigation-only mode of the fluidics control in which an irrigation valve is opened to allow either gravity or pressurized irrigation flow to reach the anterior chamber of the eye via a sleeve at the distal end of a handpiece. Foot pedal treadle position 2 correlates to an irrigation/aspiration mode of the fluidics control in which both irrigation and aspiration valves are opened to allow both fluid and cataract particles to be aspirated out of the chamber while chamber pressure is maintained using the irrigation flow. Foot pedal treadle position 3 correlates to irrigation/aspiration/ultrasound mode of fluidics and phaco control in which ultrasound energy is applied to emulsify the cataract particle whilst emulsified particles are being aspirated out of the chamber to a waste bag in the cassette. The fluidics control allows the surgeon to set either a linear or a panel setting for flow and vacuum in flow-based aspiration and vacuum in vacuum-based aspiration.

In flow-based aspiration, the fluidics control provides a capability to gradually increase or decrease aspiration flow up to the maximum flow set point by traversing the foot pedal treadle in zone 2. In vacuum-based aspiration, the fluidics control provides a capability to gradually increase or decrease aspiration vacuum up to a maximum vacuum set point by traversing the foot pedal in zone 2. When the fluidics control is set to a linear mode, the surgeon may increase or decrease fluid flow rate by varying the aspiration vacuum in a linear fashion through foot pedal treadle movement in zone 2. This requires the surgeon to actively titrate fluid flow rate and manage anterior chamber pressure during surgery through foot pedal treadle in zone 2. When the fluidics control is set to panel mode, the vacuum set point is achieved immediately when foot pedal treadle is in zone 2. In this case, a surgeon is unable to titrate the fluid flow rate. Maximum fluid flow is achieved based on the vacuum set point and irrigation head height as governed by IV pole height (set pressurized infusion point) when foot pedal treadle is traversed to zone 2.

In vacuum-based aspiration, instant availability of vacuum and higher fluid flow rates can create excellent "followability" of the cataract particles during surgery. However, higher flow rates above certain vacuum set points may create anterior chamber instability in the instance that fluid outflow exceeds fluid inflow governed by either IV pole height or pressurized irrigation source. A phacoemulsification platform that allows for the setting of fluid flow rates in conjunction with any vacuum set point in vacuum-based aspiration is needed.

SUMMARY

Various embodiments recite a surgical system, that may be used in a phacoemulsification surgical procedure, including a surgical cassette, a surgical console operatively coupled to the surgical cassette, a processor, and a display, wherein the surgical console includes a vacuum source positioned in-line with a vacuum regulator and a mass air flow controller; wherein the surgical cassette comprises a fluid volume tank connected to the mass air flow controller; wherein the processor is configured to receive a user-defined fluid flow rate setting from the display and convert the user-defined fluid flow rate setting into an air flow set point; and wherein the mass air flow controller is configured to receive the air flow set point from the processor and modulate air flow from the fluid volume tank to the vacuum source based on the user-defined fluid flow rate setting. The surgical system may further include a handpiece. In various embodiments, the mass air flow controller is further configured to modulate fluid flow rate through a tip portion of the handpiece.

Various embodiments further recite a surgical system, wherein the user-defined fluid flow rate setting includes low, medium and high set points. Various embodiments further recite a surgical system, wherein the processor is further configured to receive a user-defined vacuum set point including minimum and maximum set points. In various embodiments, the mass air flow controller is further configured to modulate air flow independent of the user-defined vacuum set point.

Various embodiments also recite a surgical system including a surgical cassette, a surgical console operatively coupled to the surgical cassette, a processor, and a display; wherein the surgical console includes a vacuum source positioned in-line with a vacuum regulator, a mass air flow controller, a mass air flow sensor, and a pressure transducer; wherein the surgical cassette includes a fluid volume tank connected in-line with the pressure transducer and the mass air flow sensor; and wherein the mass air flow sensor and pressure transducer are configured to detect a change in air flow and vacuum level from the fluid volume tank.

Various embodiments further recite a surgical system, wherein the processor is further configured to receive the detected change in air flow and vacuum level and modulate the vacuum level in the fluid volume tank to a predetermined set point, such as atmospheric pressure.

DESCRIPTION OF THE DRAWINGS

The accompanying drawings are included to provide a further understanding of the invention, and are incorporated in and constitute a part of this specification. The drawings illustrate disclosed embodiments and/or aspects and, together with the description, serve to explain the principles of the invention, the scope of which is determined by the claims.

DETAILED DESCRIPTION

Figure 1A:
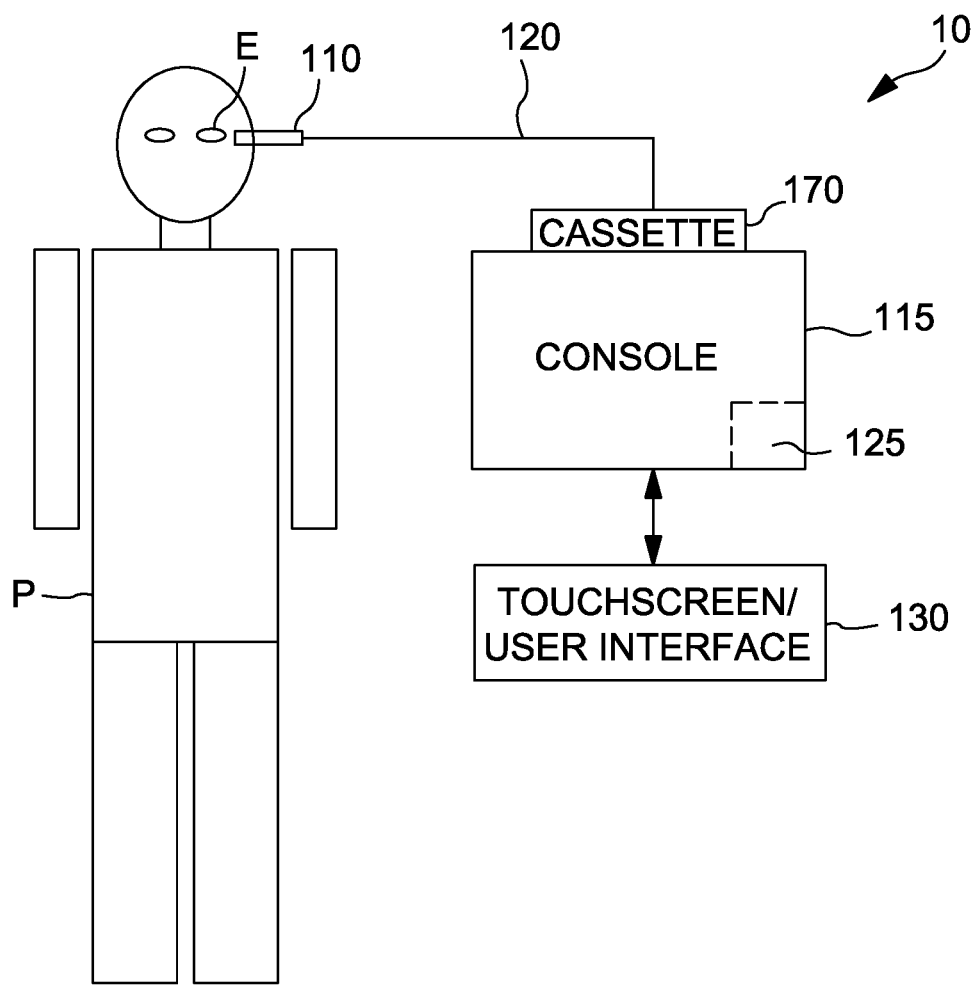
FIG. 1A is a schematic illustrating an eye treatment system in which a cassette is coupled to an eye treatment probe with an eye treatment console under one embodiment.

It is to be understood that the figures and descriptions of the present disclosure have been simplified to illustrate elements that are relevant for a clear understanding of the present invention, while eliminating, for the purpose of clarity, many other elements found in typical surgical, and particularly optical surgical, apparatuses, systems, and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

The figures and descriptions provided herein may have been simplified to illustrate aspects that are relevant for a clear understanding of the herein described apparatuses, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, for the sake of brevity a discussion of such elements and operations may not be provided herein. However, the present disclosure is deemed to nevertheless include all such elements, variations, and modifications to the described aspects that would be known to those of ordinary skill in the art.

Embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that exemplary embodiments may be embodied in different forms. As such, the exemplary embodiments should not be construed to limit the scope of the disclosure. As referenced above, in some exemplary embodiments, well-known processes, well-known device structures, and well-known technologies may not be described in detail.

In various embodiments of the system of the present disclosure, a surgical cassette, which also may be referred to as a medical pack, a fluidic cassette, or simply, a cassette, is used to facilitate irrigation and aspiration during a surgical procedure, such as phacoemulsification surgery. The surgical cassette may be inserted and mounted to a surgical console and become part of an overall phacoemulsification surgery system. The surgical cassette may perform a myriad of functions, such as effluent material collection, tube pressure sensing, and control the flow of fluid through tubing encased within the cassette and between a surgical handpiece and a surgical console.

In various embodiments of the present disclosure, the surgical cassette may include a fluid volume tank operatively coupled to a surgical console. In various embodiments, a vacuum source located in the surgical console may draw air from the fluid volume tank through an air flow controlling device, in order to modulate the rate of air flow drawn from the vacuum source.

In various embodiments, the surgical console may include a graphical user interface controller that allows a surgeon to set a desired fluid flow rate through the surgical handpiece into the eye of a patient. In various embodiments, the graphical user interface controller may also be used to allow a surgeon to set a desired vacuum setting.

In various embodiments, the system of the present disclosure is a vacuum-based aspiration system that allows a surgeon to set fluid flow rates in conjunction with a maximum vacuum setting in vacuum-based aspiration. In various embodiments, the system may provide configurable set points for fluid flow rate for a given maximum vacuum setting. In some embodiments, a proportional mass air flow controller may use this fluid flow rate set point, such as, for example, set points of low, medium, and/or high, to proportionally control the amount of air flow from a fluid volume tank in a surgical cassette to a vacuum regulating device and vacuum source. In some embodiments, the air controller acts as a variable restriction to air flow from the vacuum regulating device and the vacuum source. The fluid flow rate set point may set the air flow restriction to a desired level and result in a desired fluid flow rate for a given vacuum set point. In various embodiments, the system may be able to restrict the air flow rate at higher vacuum set points (greater than 300 mmHg) which in turn may reduce the fluid flow rate and enhance chamber stability in the eye. Although the air flow restriction rate is disclosed in some embodiments to include three settings levels (low, medium or high), in some embodiments, the air flow restriction rate may include any number of settings levels desired by the user.

Referring now to FIG. 1A, a system 10 for treating an eye E of a patient P generally includes an eye treatment probe handpiece 110 coupled with a console 115 by a cassette 170. Handpiece 110 generally includes a handle for manually manipulating and supporting an insertable probe tip. The probe tip has a distal end which is insertable into the eye, with one or more lumens in the probe tip allowing irrigation fluid to flow from console 115 and/or cassette 170 into the eye. Aspiration fluid may also be withdrawn through a lumen of the probe tip, with console 115 and cassette 170 generally including a vacuum aspiration source, a positive displacement aspiration pump, or both to help withdraw and control a flow of surgical fluids into and out of eye E. As the surgical fluids may include biological materials that should not be transferred between patients, cassette 170 will often comprise a sterilizable (or alternatively, disposable) structure, with the surgical fluids being transmitted through flexible conduits 120 of cassette 170 that avoid direct contact in between those fluids and the components of console 115.

When a distal end of the probe tip of handpiece 110 is inserted into an eye E, for example, for removal of a lens of a patient P with cataracts, an electrical conductor and/or pneumatic line (not shown) may supply energy from console 115 to an ultrasound transmitter of handpiece 110, a cutter mechanism, or the like. Alternatively, handpiece 110 may be configured as an irrigation/aspiration (I/A) and/or vitrectomy handpiece. Also, the ultrasonic transmitter may be replaced by other means for emulsifying a lens, such as a high energy laser beam. The ultrasound energy from handpiece 110 helps to fragment the tissue of the lens, which can then be drawn into a port of the tip by aspiration flow. So as to balance the volume of material removed by the aspiration flow, an irrigation flow through handpiece 110 (or a separate probe structure) may also be provided, with both the aspiration and irrigation flows being controlled by console 115.

To avoid cross-contamination between patients without incurring excessive expenditures for each procedure, cassette 170 and its flexible conduits 120 may be disposable. However, the flexible conduit or tubing may be disposable, with the cassette body and/or other structures of the cassette being sterilizable. Cassette 170 may be configured to interface with reusable components of console 115, including, but not limited to, peristaltic pump rollers, a Venturi or other vacuum source, a controller 125, and/or the like.

Console 115 may include controller 125, which may include an embedded microcontroller and/or many of the components common to a personal computer, such as a processor, data bus, a memory, input and/or output devices (including a user interface 130 (e.g. touch screen, graphical user interface (GUI), etc.), and the like. Controller 125 will often include both hardware and software, with the software typically comprising machine readable code or programming instructions for implementing one, some, or all of the methods described herein. The code may be embodied by a tangible media such as a memory, a magnetic recording media, an optical recording media, or the like. Controller 125 may have (or be coupled with) a recording media reader, or the code may be transmitted to controller 125 by a network connection such as an internet, an intranet, an ethernet, a wireless network, or the like. Along with programming code, controller 125 may include stored data for implementing the methods described herein, and may generate and/or store data that records parameters corresponding to the treatment of one or more patients.

Figure 1B:
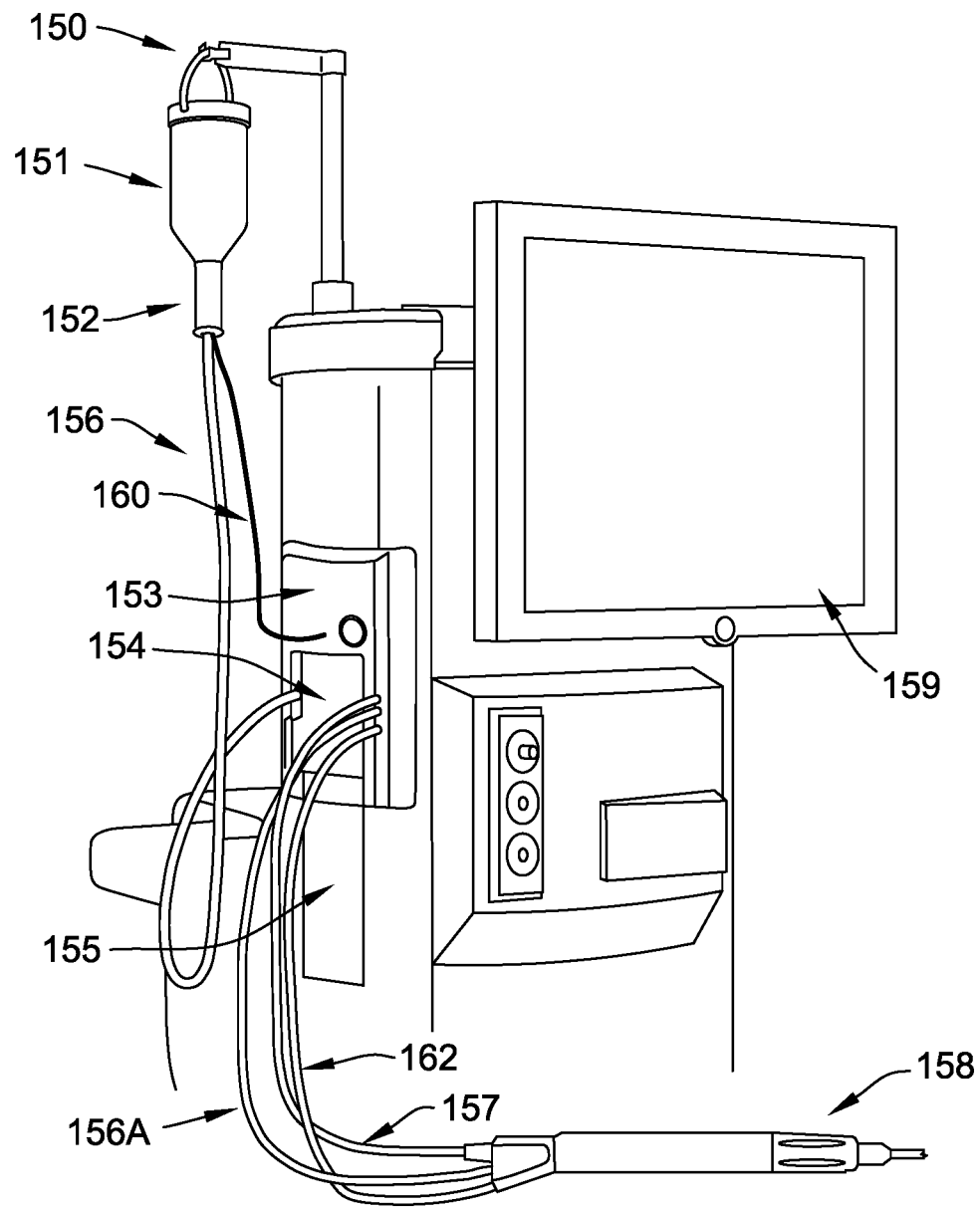
FIG. 1B is a schematic illustrating a surgical eye treatment console under another exemplary embodiment.

Referring now to FIG. 1B, a simplified surgical console is illustrated, where a fluid path may be demonstrated under an exemplary embodiment. In this example, an irrigation source 151 may be configured as a bottle or bag hanging from an IV pole hanger 150. It is understood by those skilled in the art that, while an integrated IV pole is illustrated, other configurations, utilizing standalone/static IV poles, pressurized infusion sources (for example, introducing pressurized air into irrigation source 151 via line 160), and/or other suitable configurations, are contemplated by the present disclosure.

An exemplary irrigation path for fluid may be realized via tubing cassette 154 coupled with cassette tubing interface 153, which receives fluid from irrigation source 151 via drip chamber 152. Irrigation line 156A and aspiration line 157 are coupled to handpiece 158. Irrigation fluid may flow from drip chamber 152 through the irrigation tubing 156 into tubing cassette 154. Irrigation fluid may then flow from the tubing cassette through handpiece irrigation line 156A which may be coupled to an irrigation port on handpiece 158. Aspirated fluid may flow from the eye through the handpiece aspiration line 157 back to tubing cassette 154 and into a waste collection bag 155. Handpiece 158 may also be coupled to power line 162 which may be connected to console 115. A touch screen display 159 may be provided to display system operation conditions and parameters, and may include a user interface (e.g., touch screen, keyboard, track ball, mouse, etc.—see controller 125 of FIG. 1A) for entering data and/or instructions to the system of FIG. 1B.

Figure 2A:
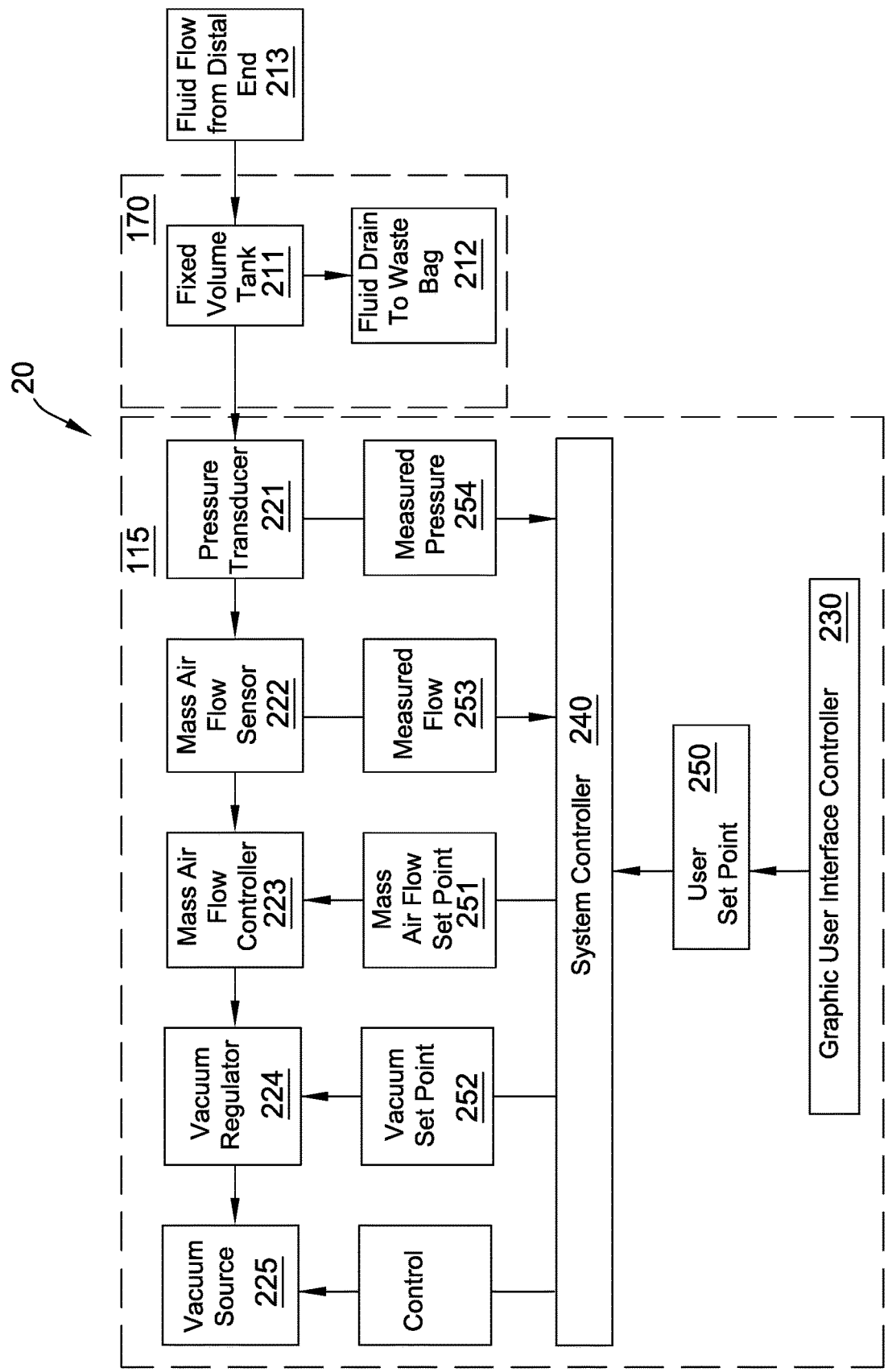
FIG. 2A is a functional block diagram of an exemplary air flow system for an eye treatment system under one embodiment, including controllers.

Referring to FIG. 2A, a functional block diagram of an exemplary air flow system 20 that may be contained within the console 115 is illustrated. The system 20 includes a cassette 170 communicatively attached to the console 115. The cassette 170 includes a fluid volume tank 211 which receives fluid flow 213 from a distal end of the handpiece 110, wherein fluid aspirated from the handpiece 110 is drained to a waste bag 212. In various embodiments, fluid from the fluid volume tank 211 is aspirated using a vacuum source 225 which is positioned in-line with a vacuum regulator 224, a mass air flow controller 223, a mass air flow sensor 222 and a pressure transducer 221. In various embodiments, the vacuum source may include one or more peristaltic pump rollers, a Venturi, or the like.

In various embodiments, as exemplified in FIG. 2A, the console 115 further includes a graphical user interface controller 230 in communication with a system controller 240. The system 20 may be configured to allow the surgeon to set a fluid flow rate in conjunction with a vacuum set point 252 using the graphical user interface controller 230. In various embodiments, the fluid flow rate may be set to a low, medium, or high set point. In various embodiments, the vacuum set point may be set in a range from a minimum to a maximum setting. The user set points 250 entered by a user via the graphical user interface controller 230 are then sent to a system controller 240, which includes a processor that may be configured to convert the fluid flow rate setting to a mass air flow set point 251 that is sent to the mass air flow controller 223. The processor is further configured to send the vacuum set point 252 to the vacuum regulator 224. In various embodiments, the vacuum regulator 224 then regulates air flow from the fluid volume tank 211 drawn by the vacuum source 225. In various embodiments, the mass air flow controller 223 simultaneously modulates the air flow from the fluid volume tank 211 so that the desired fluid flow rate flowing from the distal end of the handpiece 110 may be achieved.

In various embodiments, the mass air flow controller 223 is configured as a proportional mass air flow controller that may use the fluid flow set point (low, medium or high) entered by the user via the graphical user interface controller 230 to proportionally control the amount of air flow from the fluid volume tank 211 in the cassette 170 to the vacuum regulator 224 and vacuum source 225. In various embodiments, the mass air flow controller 223 acts as a variable restriction to air flow from the vacuum regulator 224 and the vacuum source 225.

Figure 2B:
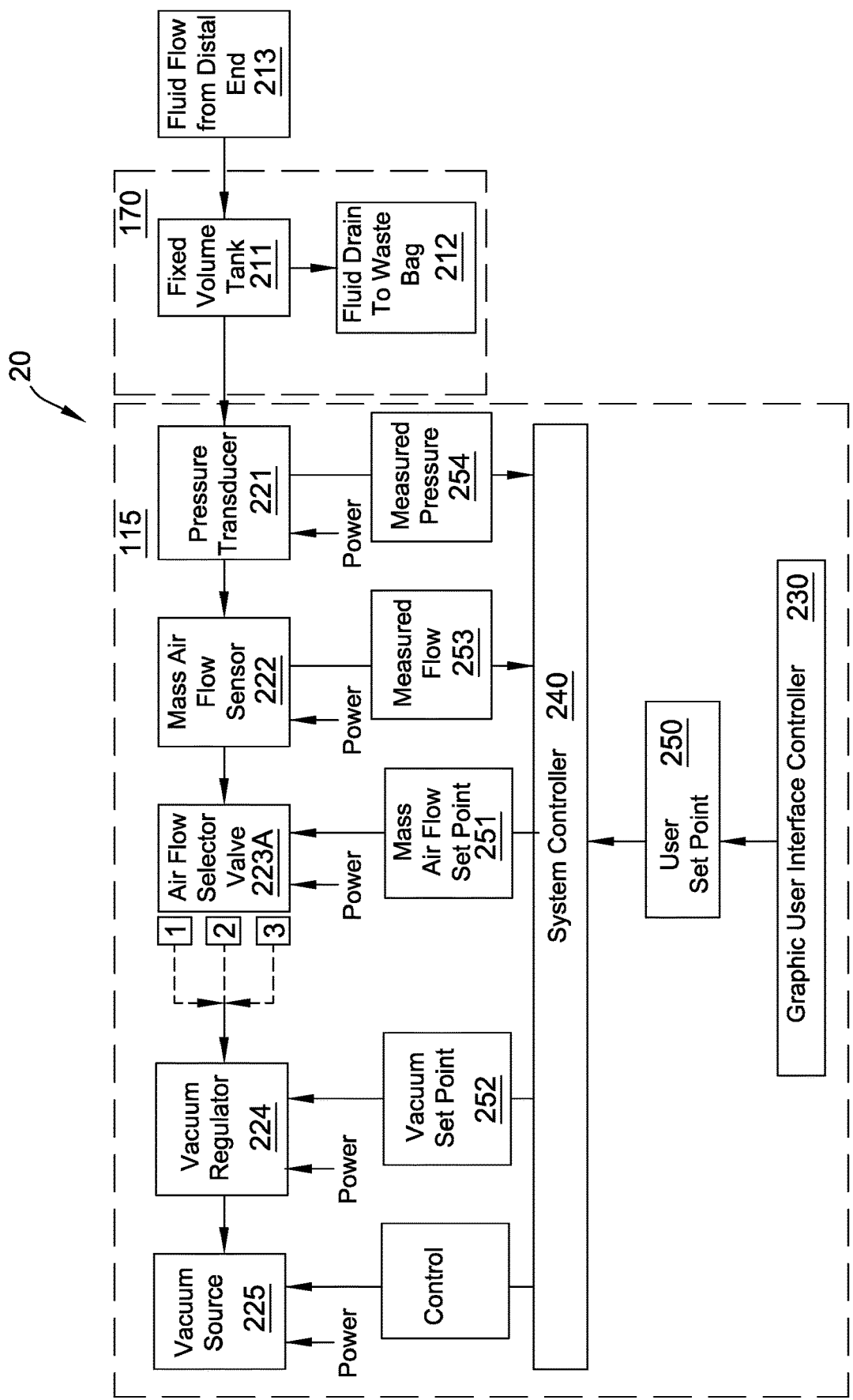
FIG. 2B illustrates another embodiment of a system of the disclosure wherein mass air flow may be controlled manually using a variable orifice including a selector valve to select an output port with a desired orifice size.

Alternatively, in some embodiments, as illustrated in FIG. 2B, the mass air flow controller 223 may be configured as a manually controlled air flow controller device 223A that functions independently of the processor. In this embodiment, the mass air flow controller 223A may be configured to be manually manipulated by the surgeon to set the air flow rate at a low (1), medium (2) or high (3) setting (user set point 250) via graphical user interface controller 230. Suitable methods of manual manipulation include manipulating levers to a low, medium or high setting, or the like.

In various embodiments, the fluid flow rate set point set by the surgeon will set the air flow restriction to a desired level and result in a desired fluid flow rate for a given vacuum set point 252. Additionally, the system 20 may be configured to restrict the air flow rate at higher vacuum set points (greater than 300 mmHg) which in turn may reduce the fluid flow rate, thus improving chamber stability. The vacuum regulator 224 (which may, for example, be electronic) will draw air from the tank 211 in the cassette 170 to reach vacuum set point 252 with given vacuum rise time. This results in significant amount of fluid outflow from distal end of the handpiece 110 at higher vacuum set points since higher set point will require larger air mass to be evacuated from the tank 211. Increased fluid flow from distal end will cause the anterior chamber pressure to drop when irrigation parameters remain constant. The proposed system can be configured such that mass air flow controller 223 will limit the amount of air flow from the tank 211 and distal end of the handpiece 110. This will cause the system to reach desired vacuum set point 252 slowly. However, this method ensures that fluid outflow from the anterior chamber is limited at higher vacuum setpoints.

In various embodiments, the amount of air flow from the fluid volume tank 211 to the vacuum regulator 224 during aspiration translates into the amount of fluid flow 213 from the distal end of the handpiece 110 to the fluid volume tank 211 while the fluid level in the fluid volume tank 211 is maintained steady by controlling the fluid drain rate to the waste bag 212 in conjunction with the mass air flow rate. In some embodiments, a low, medium or high set point for mass air flow may be set such that it may provide a needed fluid flow rate to perform a particular function using the handpiece 110.

Figure 5:
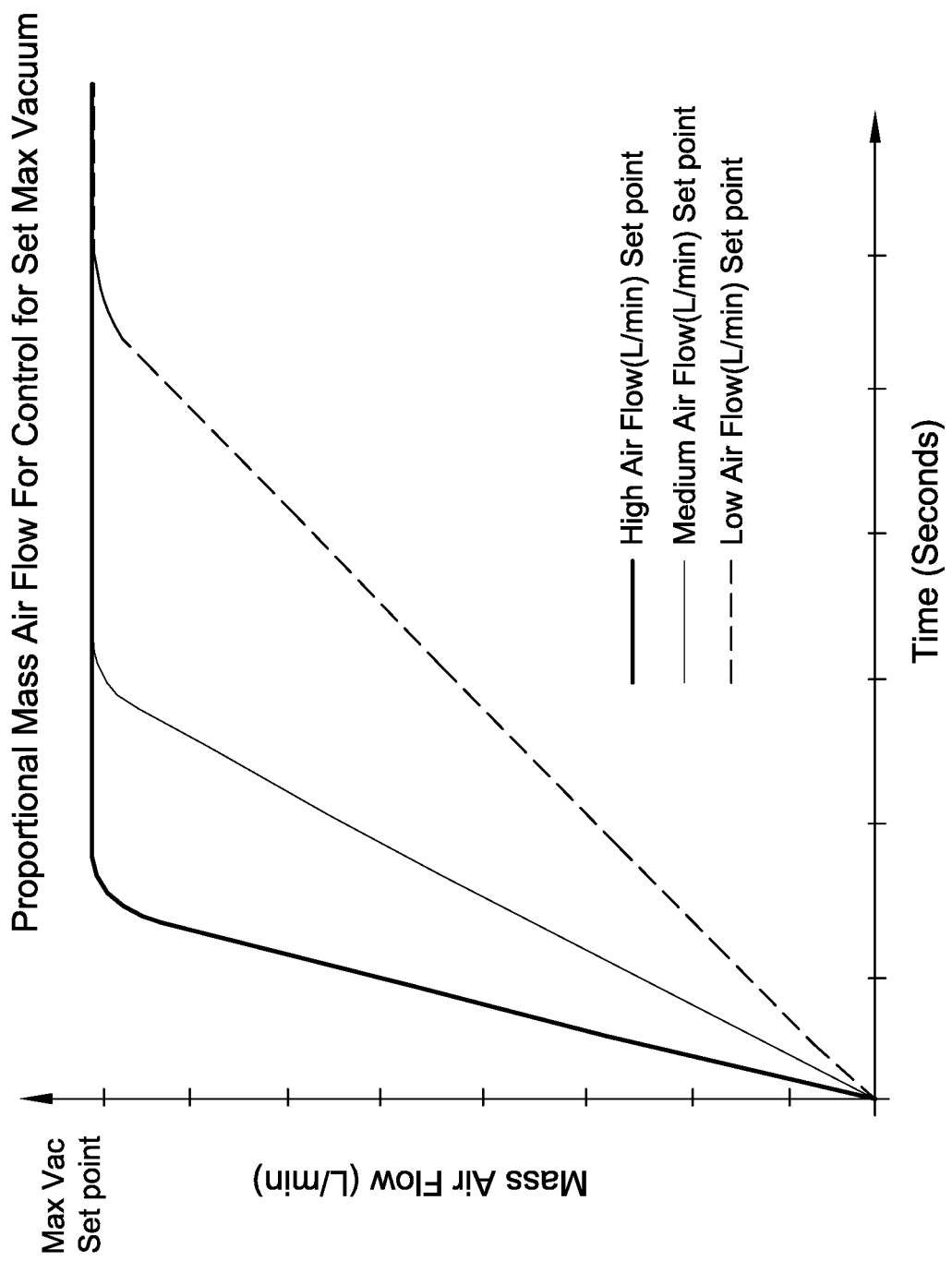
FIG. 5 illustrates a variable flow rate for a given maximum vacuum set point.

For example, a low set point for the mass air flow may be set at 20 to 24 cc/min in order to perform a Phaco Sculpt/Groove procedure at the distal end. A medium set point for the mass air flow may be set at 29 to 40 cc/min in order to perform a Phaco Chop/Epinucleus procedure at the distal end. A high set point may provide a fluid flow rate of greater than 40 cc/min up to the maximum allowed by a given vacuum set point. FIG. 5, for example, illustrates how proportional air flow control may result in a particular fluid flow rate for a given vacuum set point.

In an embodiment, as shown in FIG. 2B, the system 20 may include a mass air flow sensor 222 and a pressure transducer 221 positioned in-line with the vacuum source 225, the vacuum regulator 224 and the mass air flow controller 223. In various embodiments, the mass air flow sensor 222 and the pressure transducer 221 are configured to sense and measure a change in air flow and pressure, respectively, from the fixed volume tank 211 in the cassette 170. The measurements produced by the mass air flow sensor 222 and the pressure transducer 221 may be used to indicate an occlusion and/or an occlusion break event at the probe tip portion of the handpiece 110.

In various embodiments of the system 20, the probe tip of the handpiece 110 may become occluded, which leads to a gradual decline in mass air flow approaching a lower steady state. As shown in FIG. 2B, measured air flow parameters 253 collected from the mass air flow sensor 222 and measured pressure parameters 254 collected from the pressure transducer 221, are processed by the processor located in the system controller 240 using a predefined algorithm. The processor then signals the vacuum regulator 224 to decrease the level of vacuum in the fluid volume tank 211 to a predetermined set point. Suitable set points include atmospheric pressure. In various embodiments, decreasing the level of vacuum to a pre-determined set point may exhaust vacuum in the aspiration line and bring the pressure at a distal end of the handpiece 110 closer to atmosphere. Decreasing the level of vacuum to a pre-determined set point may also prevent an inrush of fluid from the chamber to the aspiration tubing and may mitigate effects of a post-occlusion surge event.

In various embodiments, the capability to detect a change in air flow and pressure by the mass air flow sensor 222 and pressure transducer 221 may allow for a linear rise in vacuum level after an occlusion break. In various embodiments, a linear rise in vacuum level at a particular slope (1 to 10 seconds) to a maximum set vacuum level may allow for a smoother transition to aspiration and improve chamber stability. Additionally, a linear rise may also allow a surgeon to purchase another cataract particle.

Figure 3:
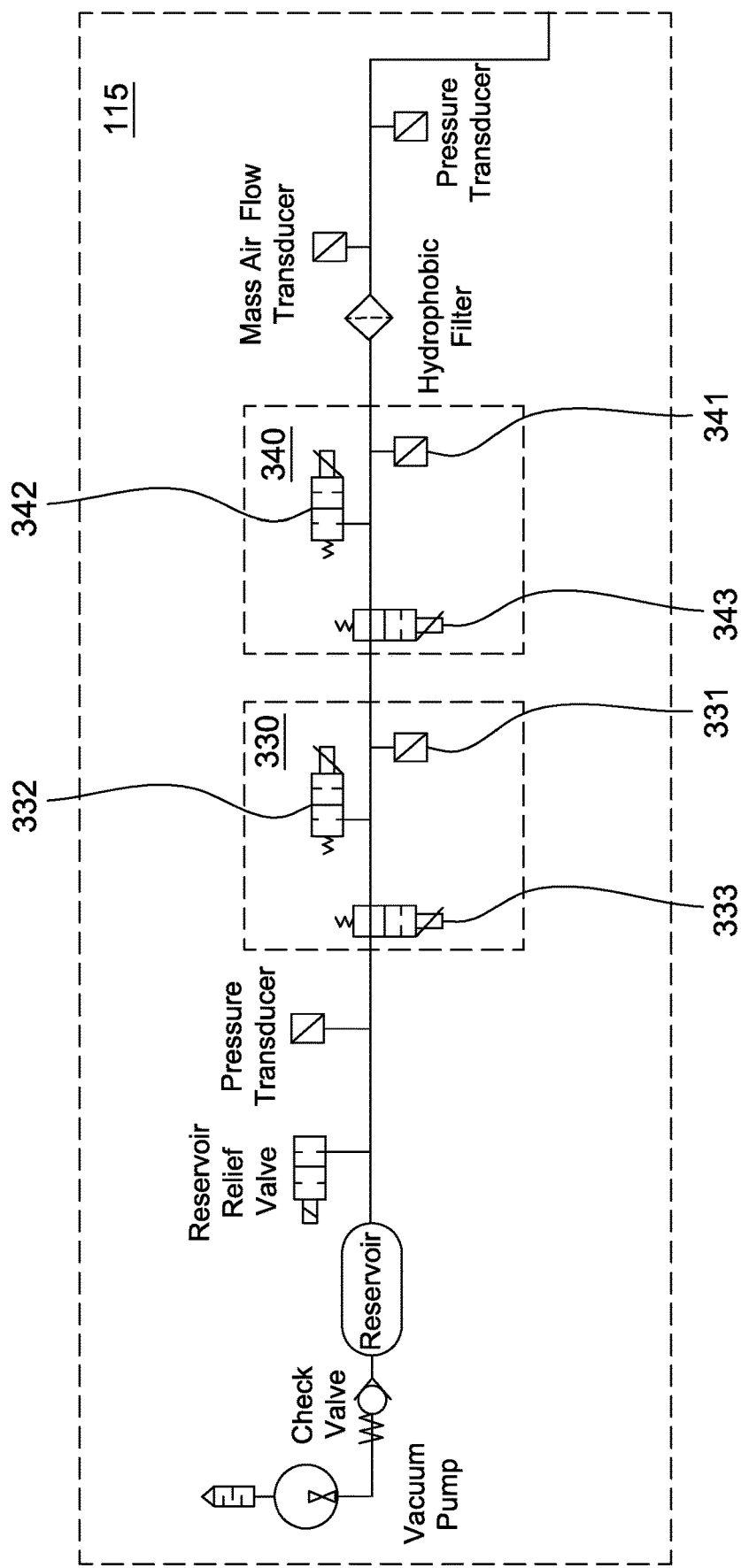
FIG. 3 is a schematic illustrating an embodiment of the air flow system of the disclosure.

FIG. 3 provides a more detailed illustration of the console 115, as well as the vacuum regulator device 330 and the mass air flow controller device 340. As illustrated in FIG. 3, the vacuum regulating device 330 includes a pressure transducer 331 at a proximal end connected to a proportional vacuum regulation vent valve 332 and a proportional vacuum regulation main valve 333 at a distal end. The mass air flow controlling device 340 includes a mass air flow transducer 341 at a proximal end connected to a proportional mass air flow vent valve 342 and a proportional mass air flow main valve 343 at a distal end.

Figure 4:
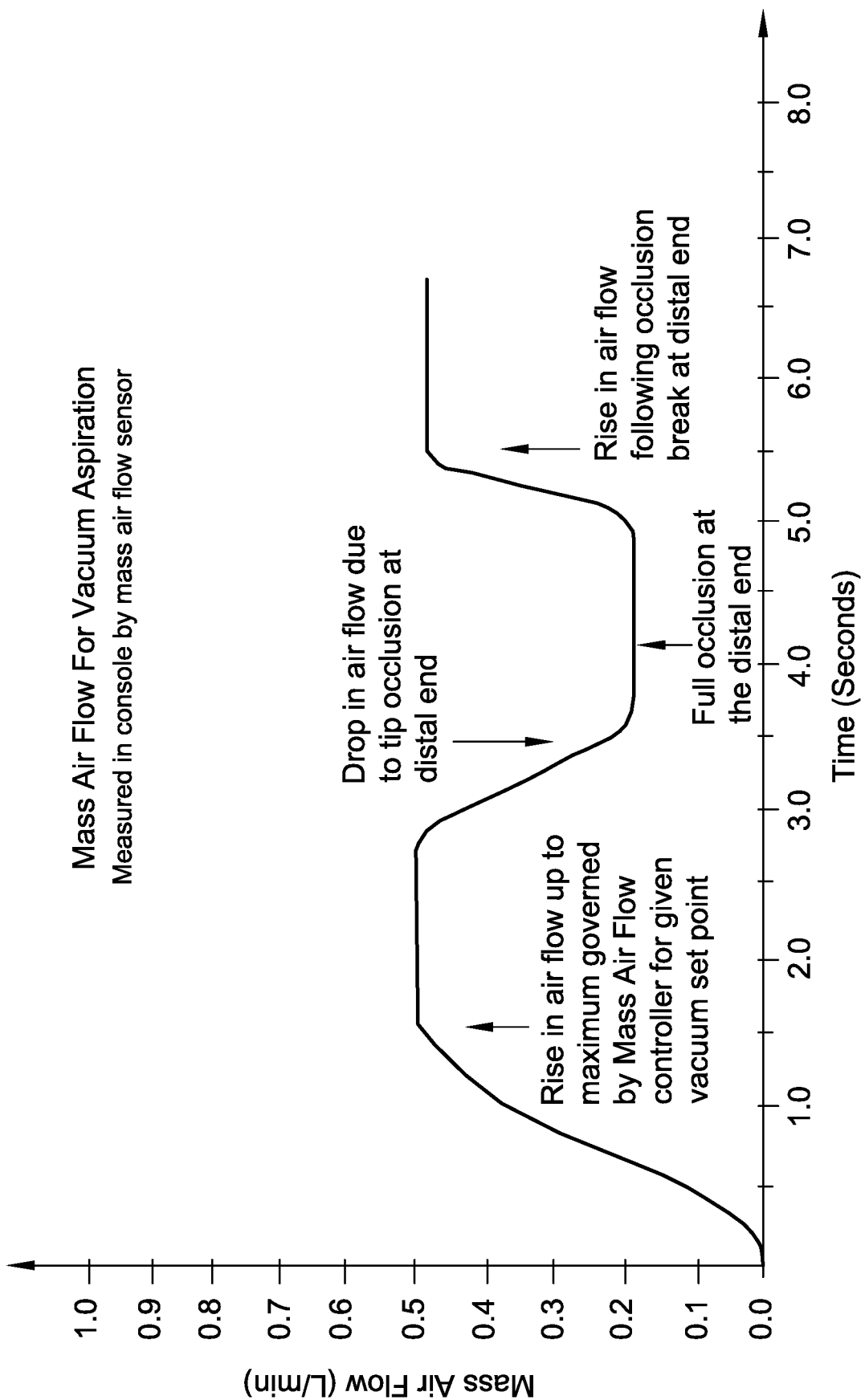
FIG. 4 illustrates a profile of mass air flow during vacuum aspiration and occlusion.

Furthermore, in various embodiments, upon occlusion break, the mass air flow may rise to a commanded set point as shown in FIG. 4, for example, where the mass air flow is measured in the console 115 by the mass air flow sensor 224. The graph in FIG. 4 illustrates an initial rise in air flow up to the maximum level governed by the mass air flow controller 223 for a given vacuum set point 252, which, in the example illustrated in FIG. 4 is 0.5 L/min. The graph then illustrates a drop in the air flow due to an occlusion of the tip of the handpiece 110 at a distal end and the mass air flow level at full occlusion at the distal end. The graph further illustrates the subsequent rise in air flow following an occlusion break at the distal end back up to the maximum level governed by the mass air flow controller 223 at a given vacuum set point 252.

Those of skill in the art will appreciate that the herein described apparatuses, engines, devices, systems and methods are susceptible to various modifications and alternative constructions. There is no intention to limit the scope of the invention to the specific constructions described herein. Rather, the herein described systems and methods are intended to cover all modifications, alternative constructions, and equivalents falling within the scope and spirit of the disclosure, any appended claims and any equivalents thereto.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather are to be accorded the widest scope consistent with the principles and novel features disclosed herein.

What is claimed is:

1. A surgical system comprising:
   a surgical cassette;
   a surgical console operatively coupled to the surgical cassette and further comprising a processor;
   a vacuum source positioned in-line with a vacuum regulator and a mass air flow controller; and
   a tank fluidly connected to the mass air flow controller;
   wherein the processor is configured to calculate an air flow set point in accordance with a received at least one user-defined vacuum set point; and
   wherein the mass air flow controller modulates air flow from the tank to the vacuum source in accordance with the received air flow set point to meet a user-defined fluid flow rate.

2. The surgical system of claim 1, wherein the surgical console further comprises a mass air flow sensor and a pressure transducer.

3. The surgical system of claim 1, wherein the user-defined vacuum set point comprises minimum and maximum set points.

4. The surgical system of claim 1, wherein the user-defined fluid flow rate setting comprises low, medium and high set points.

5. The surgical system of claim 1, wherein the air flow is about 20 to about 40 cc/min.

6. The surgical system of claim 1, wherein the mass air flow controller is further configured to modulate fluid flow rate through a handpiece.

7. The surgical system of claim 1, wherein the tank resides in the surgical cassette.

8. The surgical system of claim 1, wherein the vacuum set point is greater than 300 mmHg.

9. The surgical system of claim 1, wherein the mass air flow controller is further configured to modulate air flow independent of the user-defined vacuum set point.

10. A method of conducting surgery of the eye, the method comprising:
    providing a processor configured to calculate an air flow set point in accordance with a received at least one user-defined vacuum set point; and
    modulating air flow between a tank and a vacuum source in accordance with the received air flow set point to meet a user-defined fluid flow rate.

11. The method of claim 10, wherein the vacuum source is positioned in-line between the tank and a vacuum regulator.

12. The method of claim 10, wherein the modulating air flow is controlled by a mass air flow controller.

13. The method of claim 10, wherein the air flow is measured by a mass air flow sensor.

14. The method of claim 10, wherein the user-defined vacuum set point comprises minimum and maximum set points.

15. The method of claim 10, wherein the user-defined fluid flow rate setting comprises low, medium and high set points.

16. The method of claim 10, wherein the processor is further configured to modulate fluid flow rate through a handpiece.

17. The method of claim 10, wherein the tank resides in a surgical cassette.

18. The method of claim 10, wherein the vacuum set point is greater than 300 mm Hg.

19. The method of claim 10, wherein the air flow is about 20 to about 40 cc/min.

* * * * *